(12) United States Patent
Lin et al.

(10) Patent No.: US 11,765,806 B2
(45) Date of Patent: Sep. 19, 2023

(54) INTELLIGENT AND HEALTHY LIGHTING METHOD AND DEVICE FOR OFFICE SPACE MICRO ENVIRONMENT

(71) Applicant: TONGJI UNIVERSITY, Shanghai (CN)

(72) Inventors: Yi Lin, Shanghai (CN); Shenfei Chen, Shanghai (CN); Xianxian Zeng, Shanghai (CN)

(73) Assignee: TONGJI UNIVERSITY, Shanghai (CN)

( * ) Notice: Subject to any disclaimer, the term of this patent is extended or adjusted under 35 U.S.C. 154(b) by 0 days.

(21) Appl. No.: 17/811,057

(22) Filed: Jul. 6, 2022

(65) Prior Publication Data

US 2023/0225031 A1   Jul. 13, 2023

(30) Foreign Application Priority Data

Jan. 10, 2022   (CN) .......................... 202210018984.0

(51) Int. Cl.
*H05B 47/11* (2020.01)
*H05B 47/13* (2020.01)
*H05B 47/16* (2020.01)
*H05B 45/28* (2020.01)

(52) U.S. Cl.
CPC ............. *H05B 47/11* (2020.01); *H05B 45/28* (2020.01); *H05B 47/13* (2020.01); *H05B 47/16* (2020.01)

(58) Field of Classification Search
None
See application file for complete search history.

(56) References Cited

U.S. PATENT DOCUMENTS 9,374,867 B2 * 6/2016 Lou .................. H05B 47/10

FOREIGN PATENT DOCUMENTS

KR         102250381 B1 *  5/2021

* cited by examiner

*Primary Examiner* — Dedei K Hammond
(74) *Attorney, Agent, or Firm* — CHIESA, SHAHINIAN & GIANTOMASI PC

(57) ABSTRACT

The present disclosure relates to an intelligent and healthy lighting method and device for an office space micro environment. According to the present disclosure, high-illuminance light can be provided, according to periodic variations of human rhythms and characteristics of office time (i.e., lighting time control data), in the morning to increase rhythmic stimulation to improve alertness of office staff and working efficiency. In addition, the present disclosure effectively solves the problem that conventional lamps cannot meet the requirements of human rhythm health by setting a lighting method having multiple modes (i.e., an awake mode, a rest mode, a relax mode, a work mode, a night mode, and a silence mode) and multiple scenes (i.e., determining a lighting mode according to ambient light data, lighting time control data, and human posture data).

8 Claims, 7 Drawing Sheets

INTELLIGENT AND HEALTHY LIGHTING METHOD AND DEVICE FOR OFFICE SPACE MICRO ENVIRONMENT

CROSS REFERENCE TO RELATED APPLICATION

The patent application claims the benefit and priority of Chinese Patent Application No. 202210018984.0, filed on Jan. 10, 2022, the disclosure of which is incorporated by reference herein in its entirety as part of the present application.

TECHNICAL FIELD

The present disclosure relates to the technical field of light modulation, and in particular to an intelligent and healthy lighting method and device for an office space micro environment.

BACKGROUND ART

Light mainly acts on a visual system and a rhythm system through a visual pathway (Visual Forming System) and a non-visual neural pathway (Non-visual Forming System), and further acts on influencing factors for physical and mental health and work efficiency of office staff including emotions, etc. However, the requirements for light of the two systems are significantly different.

China's current regulations on office lighting related standards are based on the consideration of visual needs, requiring to meet "a lighting coefficient of 3.0%, a standard value of natural illuminance of 450 lx", and illuminance of an artificial lighting work surface of "300 lx or 500 lx". These regulations can already guarantee basic needs of visual work, but are not enough to stimulate biological effects and not conducive to the health of human circadian rhythms. Biorhythm disorders and emotional disorders are widely associated in pathophysiology, and studies have found that sleep quality, circadian rhythms, and emotions are highly interdependent processes. The rhythm disorders will directly lead to a decrease in the quality of human sleep or sleep disorders, resulting in emotional problems.

As one of the most important physical environmental factors in office space, light environment has a significant influence on the health level of the office staff. The light environment acts on a stress mechanism and a circadian rhythm and oxidative stress mechanism of a human body, and is significantly related to depression, cardiovascular diseases, sleep disorders, and other diseases. Chinese urban workers spend more than 80% to 90% of their time in an indoor office space in the daytime, and the long working hours and high work intensity make them more prone to fatigue and poor spirits, resulting in psychological stress and reduced work efficiency. Long-term single office light environment and low-level artificial light that is not enough to stimulate the circadian rhythms are one of the reasons for the office staff to experience sub-health status such as emotional disorders, sleep disorders, memory loss, and fatigue.

On-site research shows that a large number of open office spaces have insufficient natural light for far-window work stations. In the vast majority of office buildings, only natural lighting in the daytime causes a problem of lighting, which is reflected in too high sunlight stimulation in near-window work stations and lower light environment in the far-window work stations. However, office lighting adopts uniform light, and it is usually difficult to obtain light stimulation that can ensure the human rhythm health in the far-window work station. Also, irradiation modes and methods do not consider the difference of the individuals and the difference of operation tasks.

SUMMARY

To solve the above problems in the prior art, the present disclosure provides an intelligent and healthy lighting method and device for an office space micro environment.

To achieve the above objective, the present disclosure provides the following solutions:

An intelligent and healthy lighting method for an office space micro environment includes:

acquiring infrared sensing data, and generating human posture data according to the infrared sensing data;

determining, on the basis of the infrared sensing data, whether there is a person at a work station;

upon determining that there is a person at the work station, acquiring ambient light data, lighting time control data, and the human posture data, the ambient light data including illuminance data and light color temperature data, and the lighting time control data being set corresponding to a lighting mode;

determining the lighting mode according to the ambient light data, the lighting time control data, and the human posture data, the lighting mode comprising an awake mode, a rest mode, a relax mode, a work mode, a night mode, and a silence mode; and upon determining that there is no person at the work station within a work time period, setting the lighting mode as the silence mode.

Preferably, the step of determining the lighting mode according to the ambient light data, the lighting time control data, and the human posture data specifically includes:

determining a human sitting posture according to the human posture data, the human sitting posture including an upright sitting posture, an anteverted sitting posture, and a recumbent sitting posture;

when the human sitting posture is the upright sitting posture or the anteverted sitting posture, determining whether the ambient light data meets preset light data of the lighting mode corresponding to current lighting time control data;

if the ambient light data meets the preset light data of the lighting mode corresponding to the current lighting time control data, there is no need to change the current lighting mode; and if the ambient light data do not meet the preset light data of the lighting mode corresponding to the current lighting time control data, adjusting a lighting value until the light value is the preset light data of the lighting mode corresponding to the current lighting time control data, the light value including a lighting color temperature and a lighting intensity;

when the human sitting posture is the recumbent sitting posture, determining whether a time of the recumbent sitting posture is greater than a preset time value;

if the time of the recumbent sitting posture is greater than the preset time value, setting the lighting mode as the relax mode;

if the time of the recumbent sitting posture is less than or equal to the preset time value, determining whether the ambient light data meets the preset light data of the lighting mode corresponding to the current lighting time control data;

if the ambient light data meets the preset light data of the lighting mode corresponding to the current lighting time control data, skip changing the current lighting mode; and if the ambient light data does not meet the preset light data of the lighting mode corresponding to the current lighting time control data, adjust the lighting value until the light value is the preset light data of the lighting mode corresponding to the current lighting time control data.

Preferably, the lighting mode corresponding to first preset lighting time control data is the awake mode, the lighting mode corresponding to second preset lighting time control data and fourth preset lighting time control data is the work mode, the lighting mode corresponding to third preset lighting time control data is the rest mode, and the lighting mode corresponding to fifth preset lighting time control data is the night mode.

According to the specific embodiments provided by the present disclosure, the present disclosure discloses the following technical effects:

According to the intelligent and healthy lighting method for an office space micro environment provided by the present disclosure, high-illuminance light can be provided, according to periodic variations of human rhythms and characteristics of office time (i.e., the lighting time control data), in the morning to increase rhythmic stimulation to improve alertness of the office staff and work efficiency. In addition, the present disclosure effectively solves the problem that conventional lamps cannot meet the requirements of human rhythm health by setting a lighting method having multiple modes (i.e., an awake mode, a rest mode, a relax mode, a work mode, a night mode, and a silence mode) and multiple scenes (i.e., determining the lighting mode according to the ambient light data, the lighting time control data, and the human posture data). Moreover, personalized lighting scenes are formed according to differences of work stations and individuals, which can effectively solve the problem that the conventional lamps cannot meet the requirements of human rhythm health.

Corresponding to the intelligent and healthy lighting method for an office space micro environment provided above, the present disclosure also provides an intelligent and healthy lighting device for an office space micro environment. The device includes:

a data acquisition system configured to acquire infrared sensing data and ambient light data;

a computer analysis system connected to the data acquisition system, embedded with the intelligent and healthy lighting method for an office space micro environment provided above, and configured to generate a lighting mode adjustment instruction according to the infrared sensing data, lighting time control data, and the ambient light data, the lighting mode including an awake mode, a rest mode, a relax mode, a work mode, a night mode, and a silence mode;

a control system connected to the computer analysis system, and configured to generate a lighting drive instruction according to the lighting mode adjustment instruction; and a lighting system connected to the control system, and configured to perform lighting according to the drive instruction.

Preferably, the data acquisition system includes:

an infrared sensor connected to the computer analysis system, and configured to acquire the infrared sensing data;

an environment quality sensor connected to the computer analysis system, and configured to acquire environment temperature data and humidity data; and a light sensor connected to the computer analysis system, and configured to acquire the ambient light data.

Preferably, the intelligent and healthy lighting device for an office space micro environment further includes:

a display system connected to the computer analysis system, and configured to display the lighting mode and the environment temperature data and humidity data.

Preferably, a human-computer interaction interface is embedded in the display system for adjusting the lighting mode and light parameters.

Preferably, the intelligent and healthy lighting device for an office space micro environment further includes:

a wireless connection system separately connected to the display system and the computer analysis system, and configured to perform data interaction with an intelligent equipment, the intelligent equipment including a smartphone, a laptop, and a tablet computer.

The technical effects achieved by the intelligent and healthy lighting device for an office space micro environment provided by the present disclosure are the same as those of the intelligent and healthy lighting method for an office space micro environment provided above. Therefore, details are not described herein again.

BRIEF DESCRIPTION OF THE DRAWINGS

To describe the technical solutions in the embodiments of the present disclosure or in the prior art more clearly, the accompanying drawings required for the embodiments are briefly described below. Apparently, the accompanying drawings in the following description demonstrate only specific embodiments of the present disclosure, and the invention is not so limited.

DETAILED DESCRIPTION OF THE EMBODIMENTS

The technical solutions in the embodiments of the present disclosure will be described below clearly and completely with reference to the accompanying drawings in the embodiments of the present disclosure. Apparently, the described embodiments are merely some rather than all of the embodiments of the present disclosure. The invention is not so limited.

An objective of the present disclosure is to provide an intelligent and healthy lighting method and device for an office space micro environment. Light is modulated according to periodic variations of human rhythms and characteristics of office time to form personalized lighting scenes, thereby improving the work efficiency. Moreover, the problem that conventional lamps cannot meet the requirements of human rhythm health can be effectively solved.

To make the above-mentioned objective, features, and advantages of the present disclosure clearer and more comprehensible, the present disclosure will be further described in detail below in conjunction with the accompanying drawings and specific embodiments.

Figure 1:
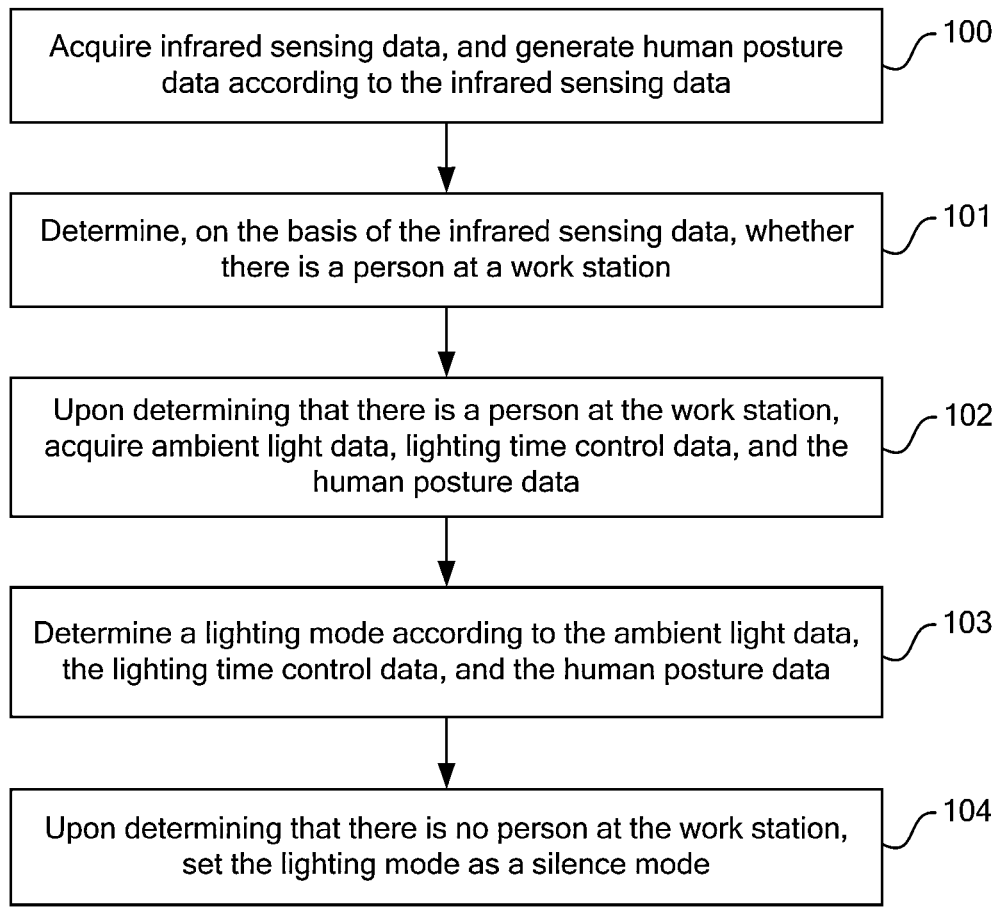
FIG. 1 is a flow diagram of an intelligent and healthy lighting method for an office space micro environment provided by the present disclosure.

As shown in FIG. 1, the intelligent and healthy lighting method for an office space micro environment provided by the present disclosure includes:

Step 100: acquire infrared sensing data, and generate human posture data according the infrared sensing data.

Step 101: determine, on the basis of the infrared sensing data, whether there is a person at a work station.

Step 102: upon determining that there is a person at the work station, acquire ambient light data, lighting time control data, and the human posture data. The ambient light data includes illuminance data and light color temperature data. The lighting time control data is set corresponding to a lighting mode. For example, the lighting mode corresponding to 8:00-10:00 (i.e., first preset lighting time control data) is set as the awake mode, the lighting mode corresponding to 10:0-12:00 (i.e., second preset lighting time control data) is set as the work mode (during which a time point and duration of the relax mode can be user-defined), the lighting mode corresponding to 12:00-13:30 (i.e., third preset lighting time control data) is set as the rest mode, the lighting mode corresponding to 13:30-17:00 (i.e., fourth preset lighting time control data) is set as the work mode (during which the time point and duration of the relax mode can be user-defined), and the lighting mode corresponding to the time after sunset of the day (i.e., fifth preset lighting time control data) is set as the night mode. The correspondence between each time period and each lighting mode can also be set according to seasons and actual work requirements, and an automatic switching duration between two lighting modes is 1 min. Specific parameters of the lighting mode can be set as follows:

Awake mode: 8000K, 800-650 lx
Rest mode: 2700K, 300 lx
Relax mode: user-defined color light, 300 lx
Work mode: 4000K, 300 lx
Night mode: amber, 150 lx
Silence mode: amber, 50 lx Step 103: determine the lighting mode according to the ambient light data, the lighting time control data, and the human posture data. The lighting mode includes the awake mode, the rest mode, the relax mode, the work mode, the night mode, and the silence mode.

Step 104: upon determining that there is no person at the work station, set the lighting mode as the silence mode.

Figure 2:
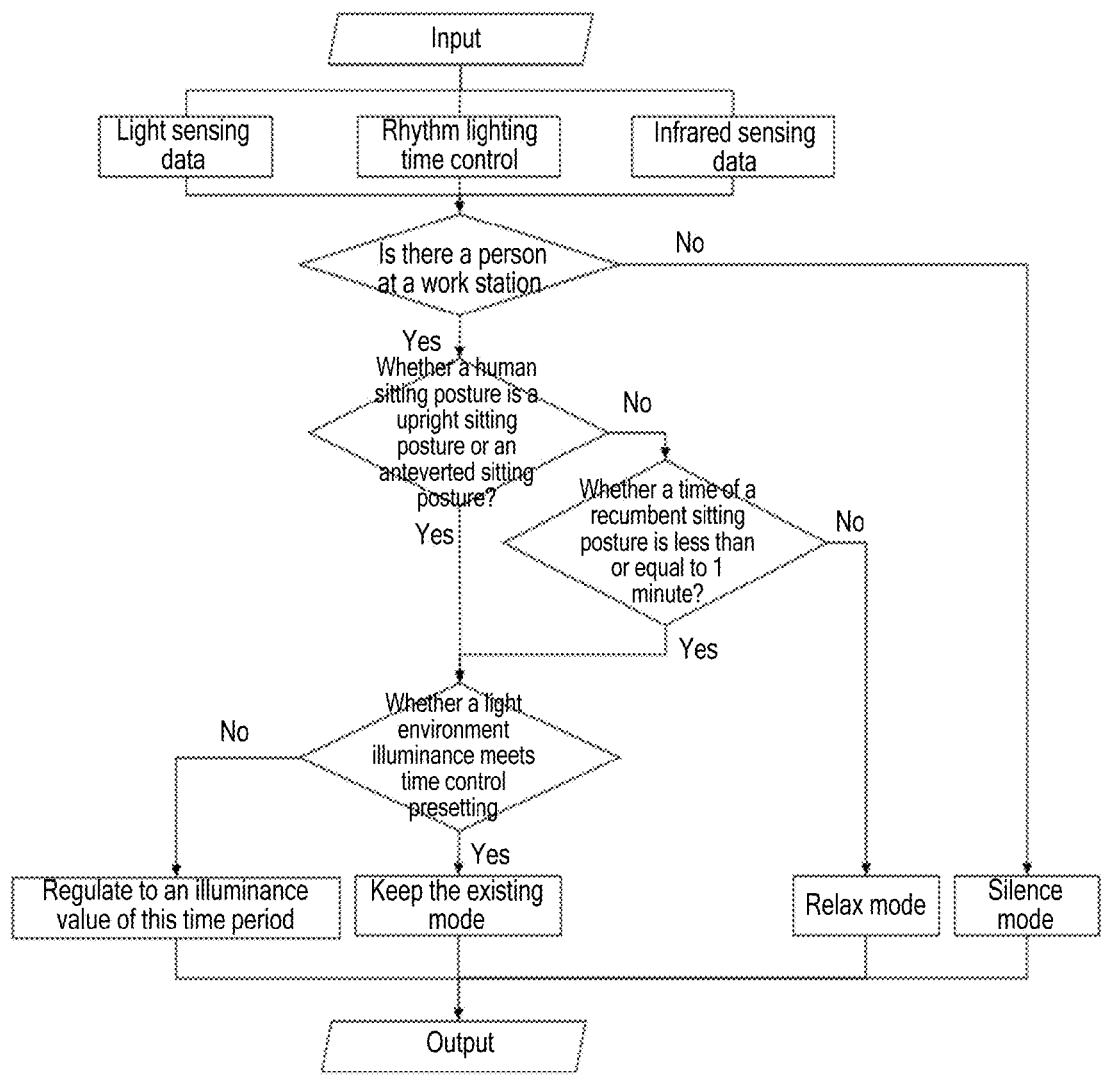
FIG. 2 is a framework diagram of implementation of an intelligent and healthy lighting method for an office space micro environment provided by the present disclosure.

As shown in FIG. 2, the specific implementation of step 103 above includes:

Determine a human sitting posture according to the human posture data. The human sitting posture includes an upright sitting posture, an anteverted sitting posture, and a recumbent sitting posture.

When the human sitting posture is the upright sitting posture or the anteverted sitting posture, determine whether the ambient light data meets preset light data of the lighting mode corresponding to current lighting time control data.

If the ambient light data meets the preset light data of the lighting mode corresponding to the current lighting time control data, not change the current lighting mode.

If the ambient light data does not meet the preset light data of the lighting mode corresponding to the current lighting time control data, adjust the lighting value until the light value is the preset light data of the lighting mode corresponding to the current lighting time control data. The light value includes a lighting color temperature and a lighting intensity.

When the human sitting posture is the recumbent sitting posture, determine whether a time of the recumbent sitting posture is greater than a preset time value. For example, in this embodiment, the preset time value is set as 1 min, but is not limited to this, and can be set by itself according to actual needs.

If the time of the recumbent sitting posture is greater than the preset time value, set the lighting mode as the relax mode.

If the time of the recumbent sitting posture is less than or equal to the preset time value, determine whether the ambient light data meets the preset light data of the lighting mode corresponding to the current lighting time control data.

If the ambient light data meets the lighting mode corresponding to the current lighting time control data, not change the current lighting mode.

If the ambient light data does not meet the preset light data of the lighting mode corresponding to the current lighting time control data, adjust the lighting value until the light value is the preset light data of the lighting mode corresponding to the current lighting time control data.

Figure 3:
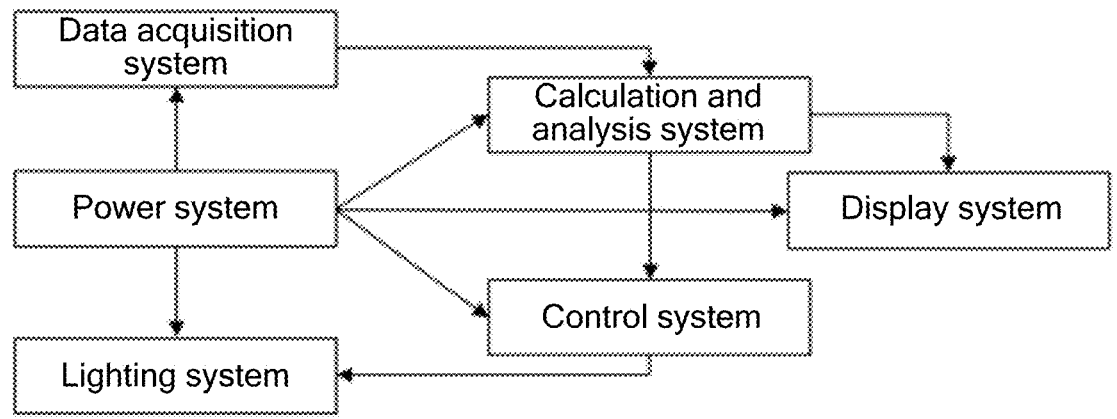
FIG. 3 is an architecture diagram of an intelligent and healthy lighting device for an office space micro environment provided by the present disclosure.

Corresponding to the intelligent and healthy lighting method for an office space micro environment provided above, the present disclosure also provides an intelligent and healthy lighting device for an office space micro environment. As shown in FIG. 3, the system includes a data acquisition system, a computer analysis system, a control system, and a lighting system.

The data acquisition system is configured to acquire the infrared sensing data and the ambient light data.

The computer analysis system is connected to the data acquisition system, embedded with the intelligent and healthy lighting method for an office space micro environment provided above, and configured to generate a lighting mode adjustment instruction according to the infrared sensing data, lighting time control data, and the ambient light data. The lighting mode includes the awake mode, the rest mode, the relax mode, the work mode, the night mode, and the silence mode. The control system is connected to the computer analysis system, and configured to generate a lighting drive instruction according to the lighting mode adjustment instruction. The lighting system is connected to the control system, and configured to perform lighting according to the drive instruction. The computer analysis system adopted in this embodiment is an intelligent chip (or a microcomputer chip), which can be provided with a time module and a data analysis module. The time module is mainly configured to acquire the lighting time control data.

To provide stable power for each system in the intelligent and healthy lighting device for an office space micro environment provided above, a power system is also provided in this embodiment. The power system adopts an electronic ballast module for converting lighting power into power required by each system of the lamp.

Figure 6:
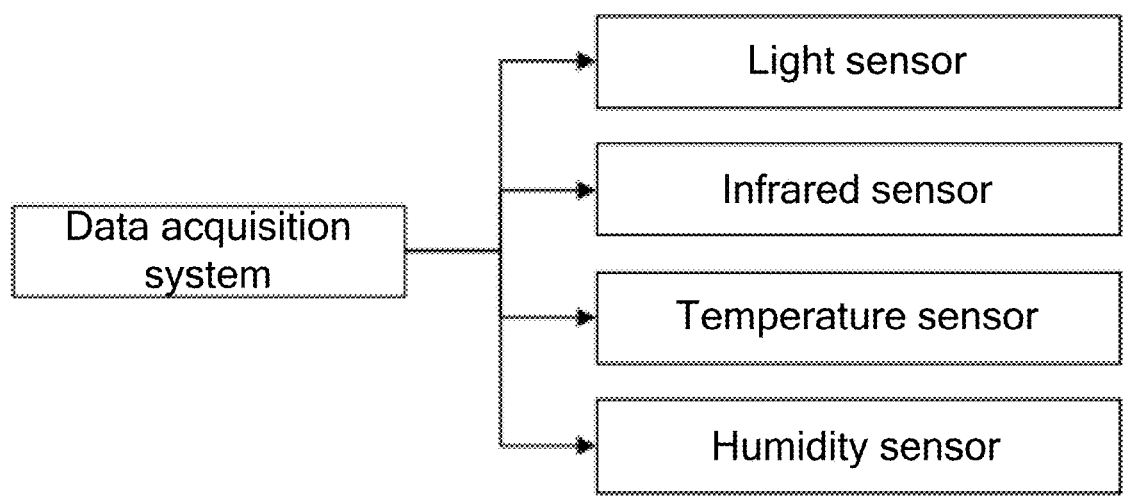
FIG. 6 is an architecture diagram of a data acquisition system provided by embodiments of the present disclosure.

As shown in FIG. 6, the data acquisition system adopted in this embodiment includes an infrared sensor, an environment quality sensor, and a light sensor. The environment quality sensor is a humidity sensor and a temperature sensor.

The infrared sensor is connected to the computer analysis system and configured to acquire the infrared sensing data. The environment quality sensor is connected to the computer analysis system and configured to acquire the environment temperature data and humidity data. The light sensor is connected to the computer analysis system and configured to acquire the ambient light data.

In the specific implementation, the light sensor acquires light environment illuminance and color temperature data of an office table micro-space.

Figure 7:
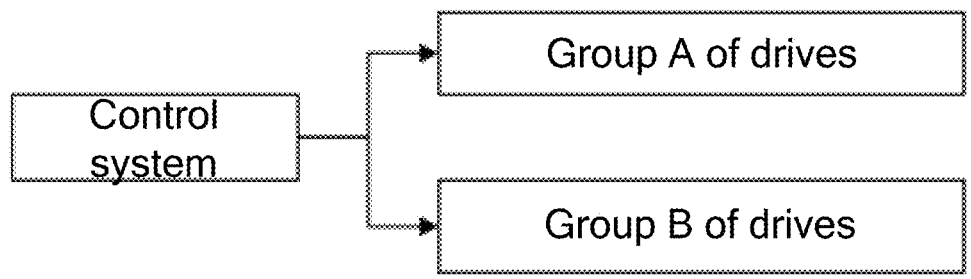
FIG. 7 is an architecture diagram of a control system provided by embodiments of the present disclosure.
Figure 8:
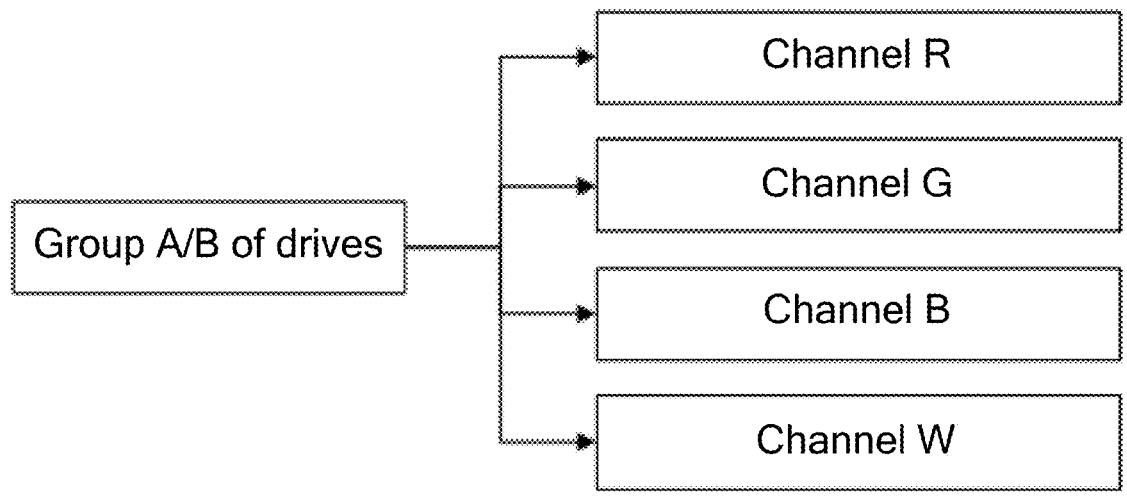
FIG. 8 is an architecture diagram of a group A of drives or a group B of drives provided by embodiments of the present disclosure.

To accurately adjust and control the illuminance, the control system adopted in this embodiment mainly refers to a control and drive module, which is configured to receive and execute an instruction issued by a calculation and analysis system 2 and mainly control the lighting system. During actual application, as shown in FIG. 7, the control system mainly includes a group A of drives and a group B of drives. As shown in FIG. 8, each group of drives includes four channels, namely R, G, B, and W.

To improve the convenience in use of the entire lighting device, a display system is also provided in this embodiment. The display system is connected to the computer analysis system and mainly configured to display the lighting mode and the environment temperature data and humidity data.

To improve the user experience, according to this embodiment, a human-computer interaction interface is also embedded in the display system for adjusting the lighting mode and light parameters. That is, the display content of the display system includes a user operation interface and displays environment quality data.

Figure 4:
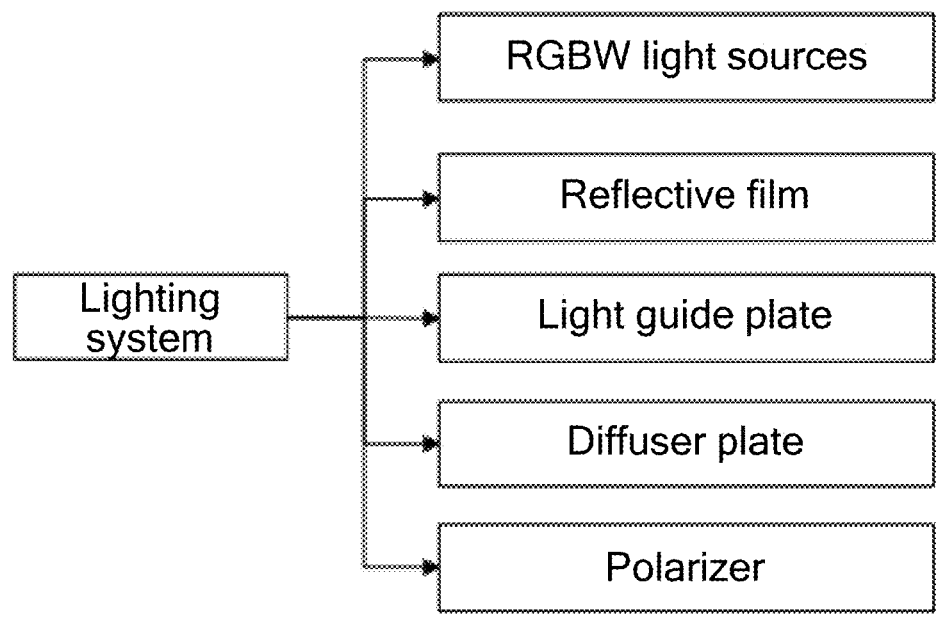
FIG. 4 is an architecture diagram of a lighting system provided by embodiments of the present disclosure.

To implement arbitrary adjustment of the light parameters, various light required for lighting is provided. As shown in FIG. 4, the lighting system adopted in this embodiment mainly includes RGBW light sources, a reflective film, a light guide plate, a diffuser plate, and a polarizer.

Figure 5:
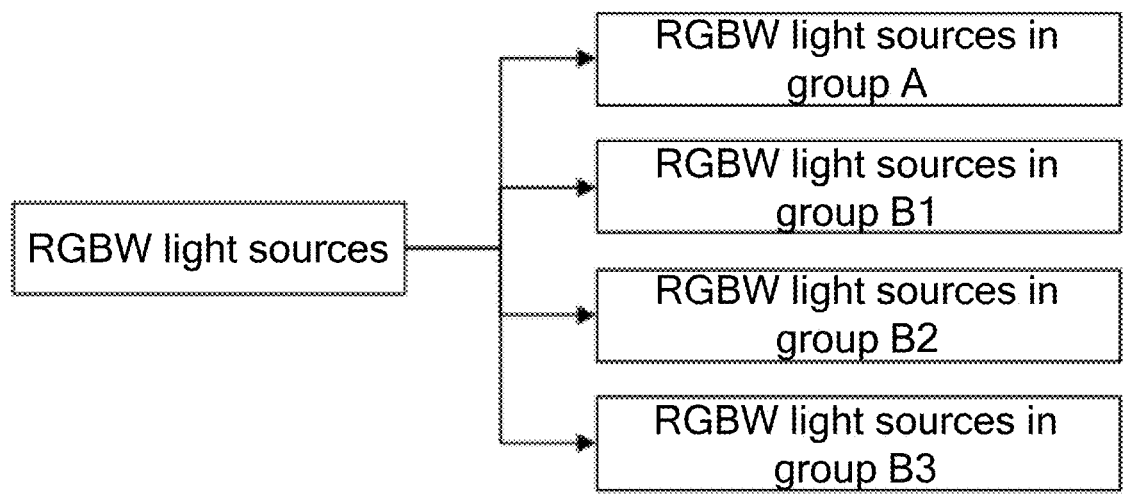
FIG. 5 is an architecture diagram of RGBW light sources provided by embodiments of the present disclosure.

The RGBW light sources are located at the upper and lower ends of the light guide plate, the polarizer is located at the forefront, and the diffuser plate, the light guide plate, and the reflective film are sequentially arranged. As shown in FIG. 5, the RGBW light sources adopt four RGBW LED arrays densely and alternately arranged to fully mix the light of the four light sources, and the overall light color and color temperature can be adjusted by adjusting a drive current ratio of the four light sources. The RGBW light sources are divided into groups A and B, the group A is on the light guide plate, and the group B is under the light guide plate. When the light emitted by the RGBW light sources passes through the light guide plate, the light is diffused to all angles by the light guide plate and then emitted from the front of the light guide plate. Various light guide points of different densities and sizes can make the light guide plate uniformly emit the light. The purpose of the reflective film is to reflect the light leaking from a bottom surface back into the light guide plate, thereby improving the use efficiency of the light. The function of the diffuser plate makes the light emitted by the light guide plate be diffused more evenly. The surface of the polarizer is optically designed to deflect the light to a tabletop and eyes of a person in a sitting posture.

For example, the awake mode is from 8:00 a.m. to 10:00 a.m. The power of 8 power sources in the group A and the group B is 100% (100% of R, 100% of G, 100% of B, 100% of W for the four channels R, G, B, and W, respectively), and the eye illuminance and the color temperature are preset as 800 lx and 8000K, respectively.

Starting from 10:00 a.m., the lighting mode is gradually switched from the awake mode to the work mode. The power of each channel of the light sources in the group A and the group B is gradually reduced from the previous 100% (100% of R, 100% of G, 100% of B, 100% of W for the four channels R, G, B, and W, respectively) to 60% (60% of R, 60% of G, 60% of B, and 60% of W).

The work mode is from 10 a.m. to 12 p.m. and from 13:30 p.m. to 17:00 p.m. The power of the light sources in the group A and the group B is 60% (60% of R, 60% of G, 60% of B, and 60% of W). During the work mode, a user can preset a user-defined relax time period through an operation interface of the display system according to self conditions. The relax time period is in the relax mode, and the light color and the light intensity of the relax mode can be selected according to self preference of the user.

The rest mode is from 12:00 p.m. to 13:30 p.m. The power of the light sources in the group A and the group B in this mode is 60% (60% of R, 60% of G, 40% of B, and 60% of W), and the eye illuminance and the color temperature are 300 lx and 2700K.

The night mode is from the time of sunset of the day to 22:00 p.m. The power of the light sources in the group A and the group B in this mode is 40% (40% of R, 40% of G, 20% of B, and 40% of W), and the eye illuminance and the color temperature are preset as 150 lx and 2300K.

Figure 11:
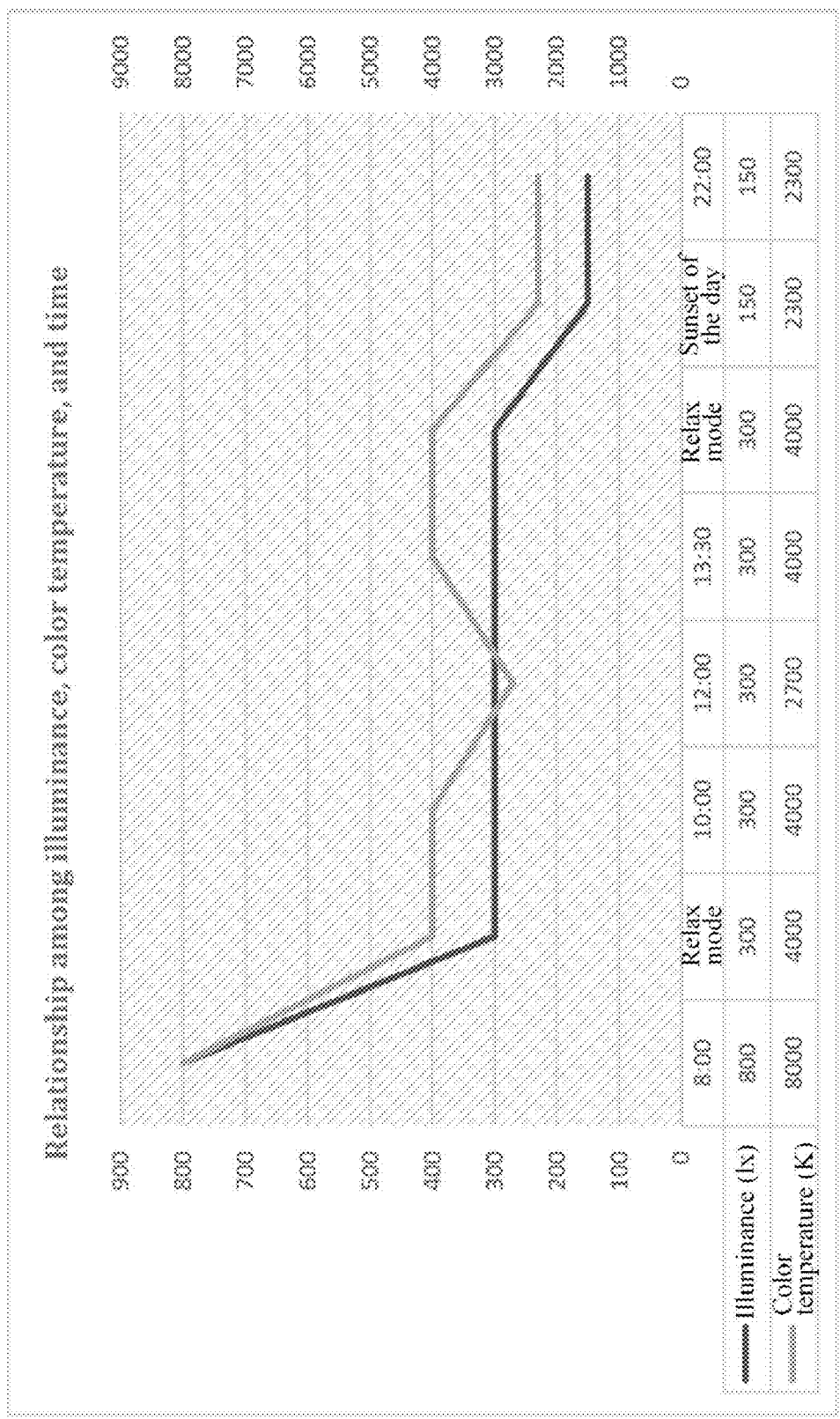
FIG. 11 is a diagram of relationship among illuminance, color temperature, and time provided by embodiments of the present disclosure.

From 8:00 a.m. to 22:00 p.m., the mode where there is no person is the silence mode. The power of the light sources in the group A and the group B in this mode is 20% (20% of R, 20% of G, 10% of B, and 20% of W), and the eye illuminance and the color temperature are preset as 50 lx and 1800K. The relationship among the color temperature, the illuminance, and the time is as shown in FIG. 11.

Figure 9:
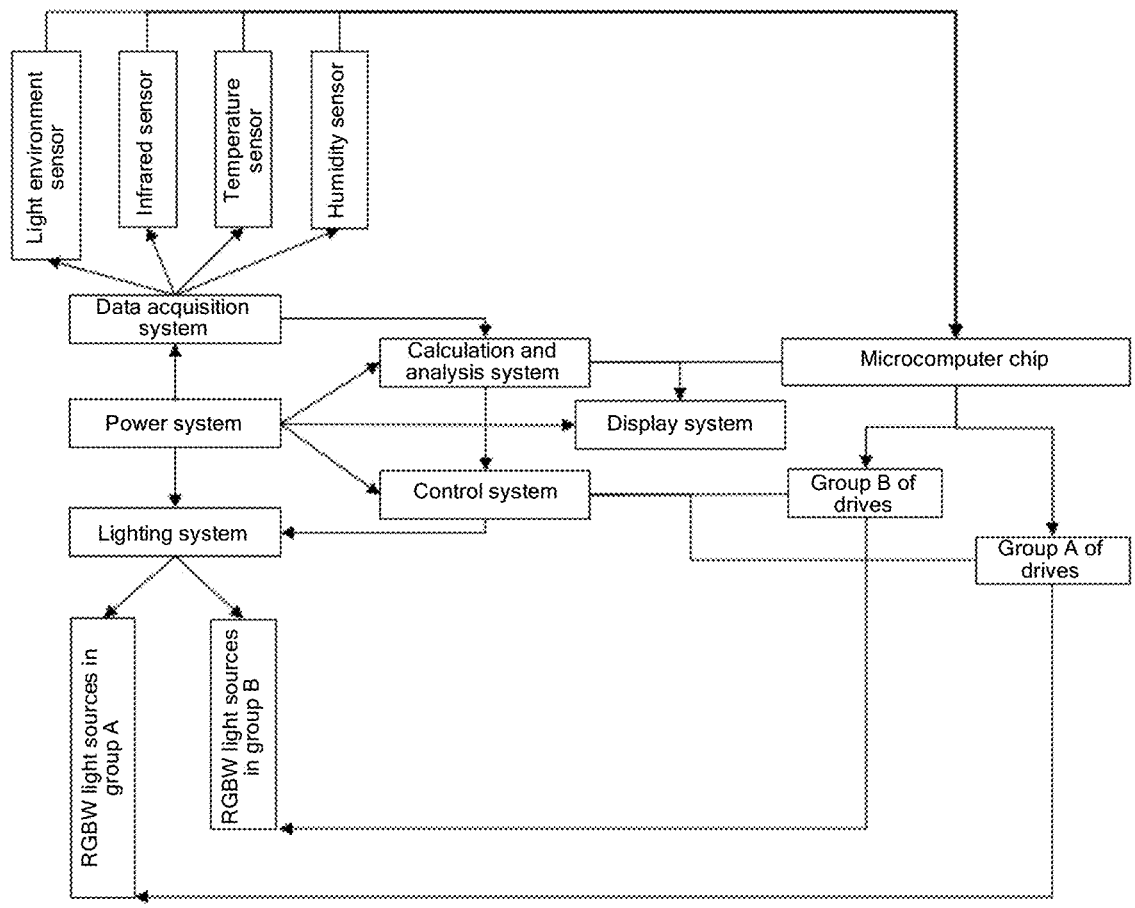
FIG. 9 is an overall architecture diagram of an intelligent and healthy lighting device for an office space micro environment provided by embodiments of the present disclosure.
Figure 10:
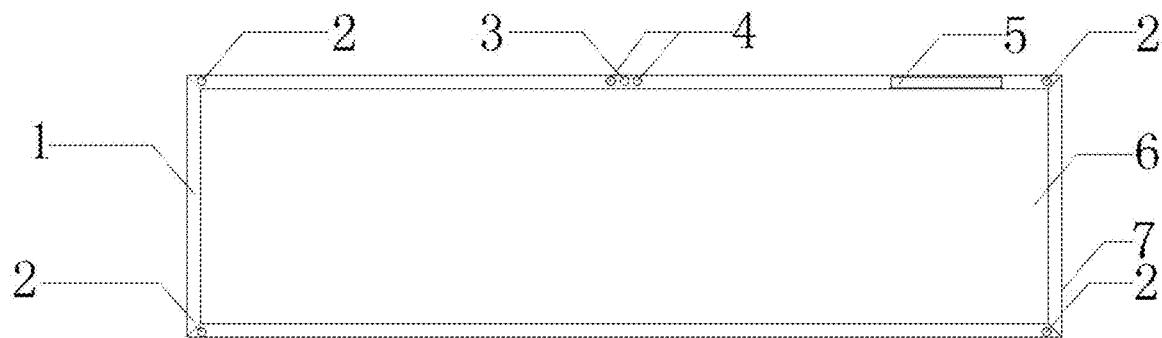
FIG. 10 is a schematic structural diagram of an intelligent and healthy lighting device for an office space micro environment provided by embodiments of the present disclosure.

On the basis of the above structure, the data acquisition system transmits the acquired environmental data to the calculation and analysis system 2, and the calculation and analysis system 2 transmits the analyzed light environment signal to the control system and transmits the analyzed environmental temperature and humidity signals to the display system 5. The control system is connected to the lighting system, and converts the received control signal into a level signal to transmit to the lighting system. The lighting system receives different level signals, lights LED lamps in different channels, and implements the control of environmental brightness. The overall architecture of the intelligent and healthy lighting device for an office space micro environment provided by this embodiment is as shown in FIG. 9, and the formed physical structure is as shown in FIG. 10. In FIG. 10, 1 represents a metal housing, 2 represents the light sensor (also called as a light environment sensor), 3 represents the environment quality sensor, 4 represents the infrared sensor, 5 represents the display system, 6 represents the lighting system, and 7 represents a light emitting component.

In addition, to further improve the convenience in use for the user, a wireless connection system is also provided in this embodiment. The wireless connection system is separately connected to the display system and the computer analysis system and configured to perform data interaction with an intelligent equipment. The intelligent equipment includes a smartphone, a laptop, and a tablet computer. This can facilitate, through an application program embedded in the intelligent equipment, the user to adjust the light parameters of the lighting system provided by this embodiment.

The specific implementation of the intelligent and healthy lighting method for an office space micro environment provided above is explained below on the basis of the intelligent and healthy lighting device for an office space micro environment provided above, and is not limited to this during the practical application.

Step 1: the time module in the calculation and analysis system starts each system.

Step 2: the light sensor in the data acquisition system detects, every half hour, the acquired ambient light illuminance data (illuminance E and color temperature K), and the presence or absence of a person at the work station and the human sitting posture data (the upright sitting posture, the anteverted sitting posture, and the recumbent sitting posture) acquired by the infrared sensor, and transmits the detected data to the calculation and analysis system. However, the detection time can also be adjusted according to actual needs.

Step 3: if the calculation and analysis system determines, according to the data of the infrared sensor, that there is a person at the work station, perform step 4; and if the calculation and analysis system determines, according to the data of the infrared sensor, that there is no person at the work station, perform step 5.

Step 4: if the calculation and analysis system determines, according to the data of the infrared sensor, that the person at the work station is in the upright sitting posture or the anteverted sitting posture, perform step 6; if the calculation and analysis system determines, according to the data of the infrared sensor, that the person at the work station is in the recumbent sitting posture, and the time is less than and equal to 1 min, perform step 6; and if the calculation and analysis system determines, according to the data of the infrared sensor, that the person at the work station is in the recumbent sitting posture, and the time is greater than 1 min, perform step 9.

Step 5: switch to the silence mode.

Step 6: upon determining, according to the ambient light illuminance data acquired by the light sensor, that the detected environment illuminance data meets the following requirement, perform step 7; and upon determining, according to the ambient light illuminance data acquired by the light sensor, that the detected environment illuminance data does not meet the following requirement, perform step 8.

The requirement is:

$$-a \le \frac{E_{detected} - \alpha \cdot E_{preset}}{\alpha \cdot E_{preset}} \le a \text{ and } -b \le \frac{K_{detected} - \beta \cdot K_{preset}}{\beta \cdot K_{preset}} \le b$$

$E_{detected}$ is a real-time illuminance value detected by the light sensor; $E_{preset}$ is a designed eye illuminance value (which can be set according to the lighting time control data); $\alpha$ is an illuminance conversion coefficient between the eyes and the light sensor; $K_{detected}$ is a real-time color temperature value detected by the light sensor; $K_{preset}$ is an eye color temperature value (which can be set according to the lighting time control data); $\beta$ is a color temperature conversion coefficient between the eyes and the light sensor; and both a and b are error coefficients and set according to actual needs between 0 and 1.

Step 7: keep the existing mode unchanged.

Step 8: the calculation and analysis system transmits a modulation signal to the control system, and the control system starts control modules A and B to modulate the four channels R, G, B, and W, so as to meet the requirement in step 6.

Step 9: switch to the relax mode.

Each example of the present specification is described in a progressive manner, each example focuses on the difference from other examples, and the same and similar parts between the examples may refer to each other.

In this specification, some specific embodiments are used for illustration of the principles and implementations of the present disclosure. The description of the foregoing embodiments is used to help illustrate the method of the present disclosure and the core ideas thereof. In addition, persons of ordinary skill in the art can make various modifications in terms of specific implementations and the scope of application in accordance with the ideas of the present disclosure. In conclusion, the content of the present description shall not be construed as limitations to the present disclosure.

What is claimed is:

1. An intelligent and healthy lighting method for an office space micro environment, comprising:
   acquiring infrared sensing data, and generating human posture data according to the infrared sensing data;
   determining, on a basis of the infrared sensing data, whether there is a person at a work station;
   upon determining that there is a person at the work station, acquiring ambient light data, lighting time control data, and the human posture data, the ambient light data comprising illuminance data and light color temperature data, and the lighting time control data being set corresponding to a lighting mode;
   adjusting the lighting mode according to the ambient light data, the lighting time control data, and the human posture data, the lighting mode selected from the group consisting of an awake mode, a rest mode, a relax mode, a work mode, a night mode, and a silence mode; and
   upon determining that there is no person at the work station within a work time period, setting the lighting mode as the silence mode.

2. The intelligent and healthy lighting method for an office space micro environment according to claim 1, wherein the step of determining the lighting mode according to the ambient light data, the lighting time control data, and the human posture data comprises:
   determining a human sitting posture according to the human posture data, the human sitting posture comprising an upright sitting posture, an anteverted sitting posture, or a recumbent sitting posture;
   when the human sitting posture is the upright sitting posture or the anteverted sitting posture, determining whether the ambient light data meets preset light data of the lighting mode corresponding to current lighting time control data;
   if the ambient light data meets the preset light data of the lighting mode corresponding to the current lighting time control data, skipping changing a current lighting mode;
   if the ambient light data does not meet the preset light data of the lighting mode corresponding to the current lighting time control data, adjusting a lighting value until the lighting value is the preset light data of the lighting mode corresponding to the current lighting time control data, the lighting value comprising a lighting color temperature and a lighting intensity;

when the human sitting posture is the recumbent sitting posture, determining whether a time of the recumbent sitting posture is greater than a preset time value;

if the time of the recumbent sitting posture is greater than the preset time value, setting the lighting mode as the relax mode;

if the time of the recumbent sitting posture is less than or equal to the preset time value, determining whether the ambient light data meets the preset light data of the lighting mode corresponding to the current lighting time control data;

if the ambient light data meets the preset light data of the lighting mode corresponding to the current lighting time control data, skipping changing the current lighting mode; and if the ambient light data does not meet the preset light data of the lighting mode corresponding to the current lighting time control data, adjusting the lighting value until the lighting value is the preset light data of the lighting mode corresponding to the current lighting time control data.

3. The intelligent and healthy lighting method for an office space micro environment according to claim 1, wherein the lighting mode corresponding to a first preset lighting time control data is the awake mode, the lighting mode corresponding to a second preset lighting time control data and a fourth preset lighting time control data is the work mode, the lighting mode corresponding to a third preset lighting time control data is the rest mode, and the lighting mode corresponding to a fifth preset lighting time control data is the night mode.

4. An intelligent and healthy lighting device for an office space micro environment, comprising:

a data acquisition system configured to acquire infrared sensing data and ambient light data, wherein the ambient light data comprises illuminance data and light color temperature data;

a computer analysis system connected to the data acquisition system, and configured to generate a lighting mode adjustment instruction according to the infrared sensing data, lighting time control data, and the ambient light data, the lighting mode selected from the group consisting of an awake mode, a rest mode, a relax mode, a work mode, a night mode, and a silence mode, and the lighting time control data being set corresponding to the lighting mode;

a control system connected to the computer analysis system, and configured to generate a lighting drive instruction according to the lighting mode adjustment instruction; and a lighting system connected to the control system, and configured to perform lighting according to the lighting drive instruction, wherein the computer analysis system comprises computer-executable instructions to perform operations comprising:

generating human posture data according to the infrared sensing data from the data acquisition system;

determining, on a basis of the infrared sensing data, whether there is a person at a work station:

upon determining that there is a person at the work station, adjusting the lighting mode according to the ambient light data, the lighting time control data, and the human posture data; and upon determining that there is no person at the work station within a work time period, setting the lighting mode as the silence mode.

5. The intelligent and healthy lighting device for an office space micro environment according to claim 4, wherein the data acquisition system comprises:

an infrared sensor connected to the computer analysis system, and configured to acquire the infrared sensing data, an environment quality sensor connected to the computer analysis system, and configured to acquire environment temperature data and humidity data; and a light sensor connected to the computer analysis system, and configured to acquire the ambient light data.

6. The intelligent and healthy lighting device for an office space micro environment according to claim 5, further comprising:

a display system connected to the computer analysis system, and configured to display the lighting mode and the environment temperature data and humidity data.

7. The intelligent and healthy lighting device for an office space micro environment according to claim 6, wherein a human-computer interaction interface is embedded in the display system for adjusting the lighting mode and light parameters.

8. The intelligent and healthy lighting device for an office space micro environment according to claim 6, further comprising:

a wireless connection system connected to the display system and the computer analysis system, and configured to interchange data with an intelligent equipment, the intelligent equipment comprising one of: a smartphone, a laptop, and a tablet computer.

* * * * *